(12) United States Patent
De Vries et al.

(10) Patent No.: US 10,709,376 B2
(45) Date of Patent: Jul. 14, 2020

(54) SYSTEM FOR SUPPORTING AN ELDERLY, FRAIL AND/OR DISEASED PERSON

(71) Applicant: KONINKLIJKE PHILIPS N.V., Eindhoven (NL)

(72) Inventors: Jan Johannes Gerardus De Vries, Leende (NL); Mirela Alina Weffers-Albu, Boukoul (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 191 days.

(21) Appl. No.: 15/575,998

(22) PCT Filed: May 26, 2016

(86) PCT No.: PCT/EP2016/061880
§ 371 (c)(1),
(2) Date: Nov. 21, 2017

(87) PCT Pub. No.: WO2016/193106
PCT Pub. Date: Dec. 8, 2016

(65) Prior Publication Data
US 2018/0146910 A1 May 31, 2018

(30) Foreign Application Priority Data
Jun. 2, 2015 (EP) .................................. 15170281

(51) Int. Cl.
*A61B 5/00* (2006.01)
*A61B 5/048* (2006.01)
*A61B 5/11* (2006.01)
*A61B 5/16* (2006.01)
*G06F 19/00* (2018.01)
(Continued)

(52) U.S. Cl.
CPC ............ *A61B 5/4082* (2013.01); *A61B 5/048* (2013.01); *A61B 5/0488* (2013.01);
(Continued)

(58) Field of Classification Search
CPC ............ A61B 5/04012; A61B 5/04014; A61B 5/04015; A61B 5/0476; A61B 5/048;
(Continued)

(56) References Cited

U.S. PATENT DOCUMENTS 8,187,209 B1    5/2012  Giuffrida
8,764,532 B1 *  7/2014  Berme ................... A61B 5/742
                                                        463/7
(Continued)

OTHER PUBLICATIONS

Bond, J.M.,: "Goal-Directed Secondary Motor Tasks: Their Effects on Gait in Subjects with Parkinson's disease", in Arch Phys Med Rehabil vol. 81, Jan. 2000, pp. 110-116.
(Continued)

*Primary Examiner* — Eugene T Wu

(57) ABSTRACT

The present invention relates to a system (10) for supporting an elderly, frail and/or diseased person (12), in particular a person suffering from Parkinson's disease, wherein the system (10) comprises: a detection unit (14) including (i) a brain activity sensor (20) for detecting a brain activity signal relating to the brain activity of the person (12) and (ii) a motion detection unit (22) for detecting a motion signal relating to a motion of one or more body parts of the person (12); an analysis unit (16) for determining, based on the detected brain activity signal and motion signal, an activity level of the person (12) which is indicative of the motoric and cognitive activity of the person (12); and a feedback unit (18) for providing a feedback to the person (12) if the activity level of the person (12) exceeds a predetermined threshold.

15 Claims, 4 Drawing Sheets

(51) Int. Cl.
*G16H 20/30* (2018.01)
*A61B 5/0488* (2006.01)

(52) U.S. Cl.
CPC .......... *A61B 5/1117* (2013.01); *A61B 5/1123* (2013.01); *A61B 5/1128* (2013.01); *A61B 5/165* (2013.01); *A61B 5/742* (2013.01); *A61B 5/7405* (2013.01); *A61B 5/746* (2013.01); *A61B 5/7455* (2013.01); *G06F 19/3481* (2013.01); *G16H 20/30* (2018.01); *A61B 5/1118* (2013.01); *A61B 2562/0219* (2013.01)

(58) Field of Classification Search
CPC ....... A61B 5/11; A61B 5/1116; A61B 5/1117; A61B 5/1118; A61B 5/112; A61B 5/1123; A61B 5/165; A61B 5/4058; A61B 5/4064; A61B 5/4082; A61B 5/4088; A61B 5/7221; A61B 5/7271; A61B 5/7282; A61B 5/746; A61B 5/0488; A61B 5/1128; A61B 5/7405; A61B 5/742; A61B 5/7455; A61B 2505/07; A61B 2562/0219
See application file for complete search history.

(56) References Cited

U.S. PATENT DOCUMENTS

| | | |
|---|---|---|
| 2005/0043774 A1 | 2/2005 | Devlin et al. |
| 2008/0045804 A1 | 2/2008 | Williams |
| 2009/0099627 A1* | 4/2009 | Molnar .............. A61B 5/04014 607/62 |
| 2012/0108998 A1 | 5/2012 | Molnar et al. |
| 2013/0060167 A1 | 3/2013 | Barkolas |
| 2013/0154827 A1 | 6/2013 | Housley |
| 2014/0240122 A1 | 8/2014 | Roberts et al. |
| 2014/0276130 A1* | 9/2014 | Mirelman .............. A61B 5/744 600/483 |
| 2015/0127265 A1 | 5/2015 | Iizuka |
| 2015/0272511 A1* | 10/2015 | Najafi ................... G16H 40/63 600/301 |

OTHER PUBLICATIONS

Morris, M. et al.: "Postural instability in Parkinson's disease: a comparison with and without a concurrent task" in Elsevier, Gait and Posture 12 (2000), pp. 205-216.

Ray, W.J., et al.: "EEG alpha activity reflects attentional demands, and beta activity reflects emotional and cognitive processes", Science, May 10, 1985: vol. 228, No. 4700, pp. 750-752.

Ray, W.J.: "EEG activity during cognitive processing: Influence of attentional factors", International Journal of Psychophysiology, vol. 3, Issue 1, Jul. 1985, pp. 43-48.

Brauer, S.G. et al., "The influence of a concurrent cognitive task on the compensatory stepping response to a perturbation in balance-impaired and healthy elders", Gait and Posture, 15, (2002) 83-93.

* cited by examiner

SYSTEM FOR SUPPORTING AN ELDERLY, FRAIL AND/OR DISEASED PERSON

CROSS-REFERENCE TO PRIOR APPLICATIONS

This application is the U.S. National Phase application under 35 U.S.C. § 371 of International Application No. PCT/EP2016/061880, filed on 26 May 2016, which claims the benefit of European Patent Application No. 15170281.8, filed on 2 Jun. 2015. These applications are hereby incorporated by reference herein.

FIELD OF THE INVENTION

The present invention relates to a system for supporting an elderly, frail and/or diseased person. In particular, the presented system focuses on supporting persons suffering from Parkinson's disease. The present invention furthermore relates to a corresponding method as well as to a corresponding computer program for carrying out said method.

BACKGROUND OF THE INVENTION

Some people, in particular elderly, frail or physically impaired people, need to be kept active but experience difficulty during physical activity. During a physical activity like walking they are at risk of falling.

The ability to carry out the "usual" everyday tasks on their own does not only depend on the age of the person, but also on various disorders which may affect walking abilities to a certain degree. Such disorders may not only affect the walking ability and the ability to perform other motoric tasks, but may also affect the cognitive capability of such persons.

Especially people suffering from Parkinson's disease are concerned with the above-mentioned problems. The risk of falling is particularly high for patients suffering from Parkinson's diseases, as their motoric and cognitive skills decline with progression of the disease. A main cause of these fall events is that patients try to do two things at once, which overloads their cognitive and motoric ability to deal with the increased workload imposed upon them by the complexity of such so termed concurrent tasks.

There are various studies that clearly show the impaired walking ability in case of concurrent tasks for patients suffering from Parkinson's disease. Bond, J. M.: "Goal-Directed Secondary Motor Tasks: Their Effects on Gait in Subjects with Parkinson's disease", in Arch Phys Med Rehabil Vol. 81, January 2000, pp. 110-116, for example, reports: "Difficulty performing two tasks at the same time is a frequent and debilitating problem in idiopathic Parkinson's disease (PD). Most people can easily talk while they are walking, write down notes while they are having a conversation on the telephone, or listen to the radio while they are driving. In contrast, many people with PD find that when they focus attention on one task, the performance of another becomes troublesome. The second task becomes slow and difficult to sustain, and in some cases cannot be performed at all. Dual task interference in PD affects both movement and cognition and is accentuated when tasks are part of a long or complex sequence". Bond, J. M. comes to the conclusion that "subjects with moderate disability in PD experience considerable difficulty when they are required to walk while attending to a complex visuomotor task involving the upper limbs".

A similar study is known from Morris, M. et al.: "Postural instability in Parkinson's disease: a comparison with and without a concurrent task" in Elsevier, Gait and Posture 12 (2000), pp. 205-216. This paper also shows in several tests that the risk of persons suffering from Parkinson's disease to unintentionally fall down while walking significantly increases if these persons perform additional concurrent cognitive and/or motoric tasks while walking and thereby get distracted.

Such persons should thus be advised to avoid doing such combined actions that combine either two motoric or a motoric and a cognitive task and then lead to an excessive demand of their cognitive and motoric skills.

US 2014/0276130 discloses methods and/or systems for diagnosing, monitoring and/or treating persons at risk for falling and/or pathological conditions.

SUMMARY OF THE INVENTION

It is an object of the present invention to provide a system which helps elderly, frail and/or diseased persons to better deal with the above-mentioned problems. It is particularly an object of the present invention to provide a system that supports persons suffering from Parkinson's disease and helps them not to get distracted by performing too many different tasks at the same time and thereby increasing their risk of falling and getting injured. It is also an object of the present invention to provide a corresponding method as well as a corresponding computer program.

In a first aspect of the present invention a system for supporting an elderly, frail and/or diseased person, in particular a person suffering from Parkinson's disease is presented. This system comprises:

a detection unit including (i) a brain activity sensor for detecting a brain activity signal relating to the brain activity of the person and (ii) a motion detection unit for detecting a motion signal relating to a motion of one or more body parts of the person;

an analysis unit for determining, based on the detected brain activity signal and motion signal, an activity level of the person which is indicative of how many different motoric and cognitive tasks the person is performing simultaneously; and a feedback unit for providing a feedback to the person if the activity level of the person exceeds a predetermined threshold.

In a further aspect of the present invention a method for supporting an elderly, frail and/or diseased person, in particular a person suffering from Parkinson's disease, is presented. Said method comprises the steps of:

a receiving a brain activity signal relating to the brain activity of the person and (ii) receiving a motion signal relating to a motion of one or more body parts of the person;

determining, based on the detected brain activity signal and motion signal, an activity level of the person which is indicative of how many different motoric and cognitive tasks the person is performing simultaneously; and providing a feedback to the person if the activity level of the person exceeds a predetermined threshold.

According to a still further aspect of the present invention, a computer program is presented which comprises program code means for causing a computer to carry out the steps of the above-mentioned method when said computer program is carried out on a computer.

Preferred embodiments of the invention are defined in the dependent claims. It shall be understood that the claimed method and the claimed computer program have similar and/or identical preferred embodiments as the claimed system and as defined in the dependent claims.

The herein presented system and method provide a possibility to actively warn persons, in particular persons suffering from Parkinson's disease, in case it is detected that they are performing too many motoric and/or cognitive tasks at the same time and therefore are at risk of falling or injuring them in another way.

The present system comprises three main components: (i) a sensing component which is herein denoted as detection unit, (ii) a processing unit which is herein denoted as analysis unit which analyses and interprets the signals sensed within the detection unit; and (iii) an actuator unit which is herein denoted as feedback unit and configured to provide a feedback to the person based on the signals processed in the analysis unit.

The detection unit may include a brain activity sensor for detecting a brain activity signal relating to the brain activity of the person and a motion detection unit for detecting a motion signal relating to a motion of one or more body parts of the person, in particular a motion of one or more limbs of the person. The detection unit may thus comprise one or more sensors which supervise the motoric and/or cognitive actions of the person.

The analysis unit is preferably realized as a processor which comprises one or more program modules which are configured to determine, based on the detected brain activity signal and motion signal, an activity level of the person which is indicative of the motoric and cognitive activity of the person. According to a preferred embodiment, the activity level is indicative of how many different motoric and cognitive tasks the person is performing simultaneously. It shall be clear that the term "determining" herein rather has the meaning of "estimating", since it is usually not possible to precisely determine e.g. based on an electroencephalography (EEG) signal and/or a movement signal, how many cognitive and/or motoric tasks a person is performing concurrently. However, it is in the present case also not that important to precisely determine the total number of tasks. It is rather important to determine based on the sensed signals whether the person is overstrained due to performing too many concurrent tasks.

The feedback unit may be steered by the analysis unit and may comprise one or more actuators that shall actively give a feedback, e.g. a warning signal, to the person if the analysis unit determines based on the detected signals that the activity level of the person exceeds a predetermined threshold.

Parkinson patients could thus be automatically warned by the herein presented system if they are walking and at the same time try to grab an item with one of their hands. In this case a warning signal could be produced that may warn the person to focus on walking. This may reduce the risk of falling and especially create awareness of how important it is that the person focuses on one task and does not get distracted by performing several tasks at the same time.

In the following, some terms which are used throughout the application, shall be shortly explained and defined:

The term "activity level of the person" shall be a measure for the amount of cognitive activity that is detected based on the brain activity signal and/or the amount of motion that is detected based on the motion signal. The activity level is preferably a measure which is indicative of how many different motoric and/or cognitive tasks the person is performing simultaneously. Hence, the activity level of the person shall be a measure that describes the cognitive effort of the person and/or how much and fast he/she is moving or how many limbs and body parts are moved at the same time. The activity level may be expressed as a certain value that is measurable on a scale, but it may also comprise several qualitative and/or quantitative parameters.

The term "predetermined threshold" may be a concrete value or condition which is predefined in the analysis unit as condition to steer the feedback unit to provide a feedback to the person if the activity level exceeds said value or meets the predefined condition.

The term "motoric task" is equivalent to a predominantly motoric action that is performed by the person involving voluntary movement of (part of) his/her body. Typical motoric tasks are walking, standing up from sitting, grabbing an item with a hand, carrying an item with a hand, etc.

The term "cognitive task" shall refer to any predominantly cognitive action performed by the person. Typical cognitive tasks are reading a book, unraveling a mystery, solving a mathematical problem or puzzle, thinking about a person, making a planning for the day, etc.

Of course, there are also combined cognitive and motoric tasks such as speaking with gestures, musical improvisation (e.g., jazz).

According to an embodiment, the brain activity signal may include a plurality of different signal components each relating to the brain activity in a different region of the brain of the person, wherein the analysis unit is configured to determine the activity level of the person by analyzing the different signal components in order to estimate how many different motoric and cognitive tasks the person is performing simultaneously.

The brain activity sensor may, for example, include several sensors, wherein each one supervises a different brain region of the person. The term "signal component" may thus relate to different partial signals that are provided by the separate sensors of the brain activity sensor. It may also relate to different signal channels. One sensor may, for example, supervise the primary motor cortex, another one the premotor cortex, a further one the prefrontal area, and a still further one the posterior parietal cortex of the person.

The brain activity in the primary motor cortex typically relates to a currently ongoing movement of the person. The brain activity in the premotor cortex could be measured to detect the intention to perform a movement (this brain region is typically active just before the movement is initiated). To detect cognitive activity, focus can be given to the prefrontal cortex where decision making and reasoning typically takes place and working memory is located as well as the area for speech production.

According to an embodiment, the analysis unit may, for example, be configured to consider the activity level of the person as exceeding the predetermined threshold and to steer the feedback unit to provide the feedback if a first one of the different signal components which relates to the brain activity in a first region of the brain of the person indicates a brain activity in said first region above a first predetermined brain activity level.

For example, the activity level could be regarded as exceeding the predetermined threshold if the brain activity detected in the primary motor cortex is above a predetermined threshold indicating that the person is currently performing several motoric tasks concurrently.

The analysis unit may also be configured to consider the activity level of the person as exceeding the predetermined threshold and to steer the feedback unit to provide the feedback if a first one of the different signal components which relates to the brain activity in a first region of the brain of the person indicates a brain activity in said first region above a first predetermined brain activity level and if simultaneously a second one of the different signal components which relates to the brain activity in a second region of the brain of the person indicates a brain activity in said second region above a second predetermined brain activity level.

In other words, the predetermined threshold of the activity level could be regarded as being exceeded if it is detected that the brain activity in two brain regions of the person is simultaneously at a comparatively high level. The terms "first" and "second" (signal component, region of the brain, predetermined brain activity level) is herein not used to imply any chronological order or preference list, but just to distinguish between different parts that are herein named by the same term. The activity level of the person may, for example, be regarded to exceed the predetermined threshold (such that a feedback to the person is necessary) if the brain activity in the primary motor cortex is above a predefined level and the brain activity in the premotor cortex is at the same time also above a predefined (other) level. Such a situation could indicate that the person is currently moving, e.g. walking, and at the same time intends to make another motoric task, e.g. to grab an item from a desk. The system would then warn the person by means of a feedback signal not to make too many tasks at the same time.

The activity level of the person could also be regarded as exceeding the predetermined threshold if it is detected that the brain activity in the primary motor cortex is above a predetermined level and the brain activity in the prefrontal cortex is at the same time above a predetermined (other) level. Such a situation could e.g. be an indicator that the person tries to speak while walking.

In summary, in the above-mentioned embodiments it is possible to create from the different signal components of the brain activity signal a measure of brain activity in certain areas of the brain and to reconstruct a kind of 2D/3D heat map of the person's brain. It is then possible to retrieve per selected area of the brain the brain activity (e.g. by taking the integral over that area). The system could warn the person if the brain activity in a specific area is fairly high or the brain activity in two different brain areas is at a comparatively high level at the same time.

According to a further embodiment, the system may further comprise a memory unit for storing a reference brain activity signal, wherein the analysis unit is configured to determine the activity level of the person by comparing the brain activity signal detected by the brain activity sensor with the reference brain activity signal stored in the memory unit.

The above-mentioned reference brain activity signal is preferably a brain activity signal that is recorded while the person is at rest, i.e. not moving and not actively performing any cognitive tasks. This reference brain activity signal may be acquired and stored in the memory unit during an initialization phase. The system may then compare the currently measured brain activity signal or the different components of the brain activity signal relating to the different brain areas of the person to the one or more reference brain activity signals stored in the memory unit. The predetermined threshold of the activity level could then be defined as a certain fixed value, e.g. 2, 3 or 4 and be defined as the quotient of the currently measured brain activity signal divided by the reference brain activity signal. The predetermined threshold could, for example, be regarded as being exceeded if the maximum amplitude or the total signal power of the currently measured brain activity signal is twice as high as the maximum amplitude or the total signal power of the reference brain activity signal. Of course, this comparison may again be done for the brain activity in separate brain regions or for the overall brain activity of the whole brain.

Similarly, a reference motion signal may also be stored in the memory unit, and the analysis unit may be configured to determine the activity level of the person by comparing the detected motion signal with the reference motion signal.

The analysis unit may e.g. be configured to determine, based on the detected motion signal, how the person is walking and to compare it to the normal gait of the person in order to detect deviations from the normal gait. The motion signal reflecting the normal gait of the persons could be stored in the memory unit as reference motion signal. The analysis unit may in this case be configured to steer the feedback unit to provide a feedback to the patient if it is detected that the gait differs from the normal gait of the person, i.e. if it is detected that the detected motion signal differs from the reference motion signal stored in the memory unit.

According to a further embodiment, the brain activity sensor is an EEG sensor and the brain activity signal is an EEG signal, and wherein the analysis unit is configured to determine the activity level of the person by analyzing the EEG signal in one or more ranges of the frequency spectrum of the brain activity signal in the frequency domain.

The analysis unit may, for example, be configured to analyze at least one of (i) a signal power in the whole frequency spectrum of the EEG signal, (ii) a signal power in the alpha band of the EEG signal and (iii) a signal power in the beta band of the EEG signal.

In this context the term "signal power" relates to the area under the curve of the frequency spectrum, e.g. by taking an integral over a certain frequency band.

The EEG signal may, for example, be transferred from the time domain into the frequency domain by performing a Fourier Transform. Considering the signal power in the whole frequency spectrum of the brain activity signal between 0 and 100 Hz may relate to the total brain activity. High levels of this total signal power are expected in case the person is performing a plurality of cognitive and/or motoric tasks at the same time. On the other hand, considering the signal power in the alpha band (7.5-12.5 Hz) may deliver an indication regarding the motoric tasks the person is performing. Low levels in the alpha band are expected in case of a high motoric and/or cognitive activity of the person. High levels in the alpha band are on the other hand associated with relaxation. A further reasonable measure is the analysis of the beta band (12.5-40 Hz) of the brain activity signal in the frequency spectrum. High signal power in the beta band is usually linked to active cognitive processes and may be an indicator of high cognitive efforts of the person. These and other correspondences between the different ranges of the frequency spectrum of an EEG signal and the motoric and/or cognitive activity of a person were also shown in several experiments performed in the following two scientific papers, the contents of which are herein incorporated by reference: Ray, W. J., et al.: "EEG alpha activity reflects attentional demands, and beta activity reflects emotional and cognitive processes", Science, 10 May 1985: Vol. 228, No. 4700, pp. 750-752 and Ray, W. J.: "EEG activity during cognitive processing: Influence of attentional factors", International Journal of Psychophysiology, Vol. 3, Issue 1, July 1985, pp. 43-48.

The analysis unit may be configured to consider the activity level of the person as exceeding the predetermined threshold and to steer the feedback unit to provide the feedback if at least one of (i) the signal power in the whole frequency spectrum of the EEG signal is above a first threshold value, (ii) the signal power in the alpha band of the EEG signal is below a second threshold value, and/or (iii) the signal power in the beta band of the EEG signal is above a third threshold value.

It shall be noted that in the foregoing the focus was mainly on the sensing based on the brain activity signal. As laid out above, this enables to evaluate both cognitive and motoric activity. However, it is especially preferred if the detection unit combines both the brain activity sensor and the motion detection unit (motion sensors), since such a combination enables a more reliable sensing of the motoric tasks.

According to a further embodiment, the analysis unit may be configured to determine, based on the detected brain activity signal and motion signal, whether the person is walking, and wherein the analysis unit is configured to consider the activity level of the person as exceeding the predetermined threshold and to steer the feedback unit to provide the feedback if it is determined, based on the detected brain activity signal and motion signal, that the person is walking and simultaneously performing an additional motoric and cognitive task.

As mentioned in the beginning, especially persons suffering from Parkinson have great difficulties with walking. The risk of falling increases significantly if such persons do not focus on walking, but perform other tasks (cognitive and/or motoric tasks) at the same time. The system in this configuration is especially targeted on detecting such situations and providing a feedback to the person if such a situation is detected, e.g. if it is detected that the person is walking and at the same time trying to grab an item with his left hand. In the easiest case, such situations may be detected by means of movement sensors that are attached to the limbs (left leg, right leg, left arm, right arm) of the person. If combined with an EEG sensor, the measurement can be performed even more reliable.

The motion detection unit may comprise one or more accelerometers. These accelerometers may be attached to several body parts of the person, in particular to the limbs of the person. They may then measure the accelerations at these body parts which gives an indication of how the person is moving.

Alternatively or additionally, the motion detection unit may comprise an optical motion sensor. Such an optical motion sensor may, for example, be embodied as a video camera that films the person and records the movement of specific body parts of the person.

Still alternatively or additionally, the motion detection unit may comprise an electromyography (EMG) sensor. Such an EMG sensor measures the electrical activity within the muscles and nerves and may also give an indication regarding the type and amount of movement of the person. The EMG sensor or the EMG sensors would also be preferably arranged at the limbs of the person.

As already mentioned before, the brain activity sensor preferably comprises an electroencephalography (EEG) sensor. Alternatively or additionally, the brain activity sensor may also comprise a functional magnetic resonance imaging (fMRI) sensor and/or one or more heat sensors which are configured for thermal sensing of the head, as increased cognitive effort usually increases the blood flow and thereby the heat released by that part of the brain. However, it shall be noted that for the herein described application, very sensitive heat sensors would have to be used. The accuracy would of course also be limited compared to the usage of an EEG sensor.

The feedback unit may comprise at least one of (i) a loudspeaker for providing an audible feedback to the person, (ii) a display or light actuator for providing a visual feedback to the person, and (iii) a tactile actuator for providing tactile feedback to the person. Care should be taken in choosing the actuator signals to avoid startling the person and thereby cause the person to loose his/her balance. However, generally any type of feedback is conceivable that allows the person to become aware to change his/her behavior and avoid performing concurrent tasks.

BRIEF DESCRIPTION OF THE DRAWINGS

These and other aspects of the invention will be apparent from and elucidated with reference to the embodiments described hereinafter. In the following drawings

FIG. 5 shows an exemplary EEG signal in the time domain, wherein FIG. 5a shows the delta band, FIG. 5b the theta band, FIG. 5c the alpha band and FIG. 5d the beta band of the EEG signal;

DETAILED DESCRIPTION OF THE INVENTION

Figure 1:
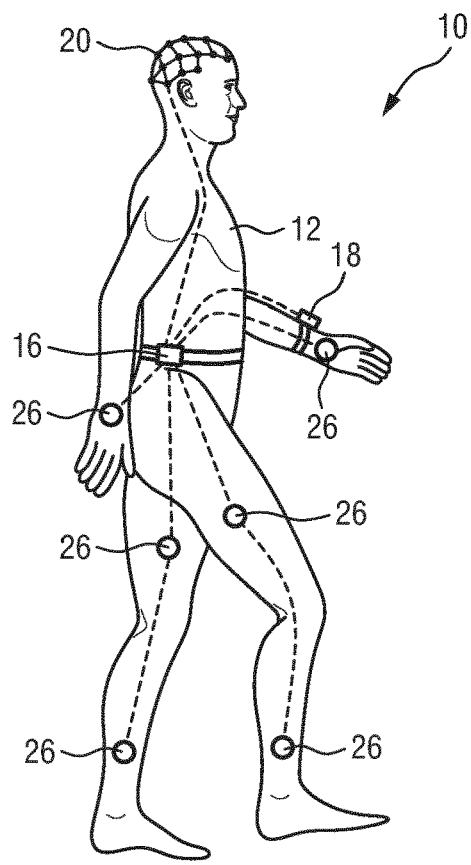
FIG. 1 shows a first embodiment of a system according to the present invention.
Figure 2:
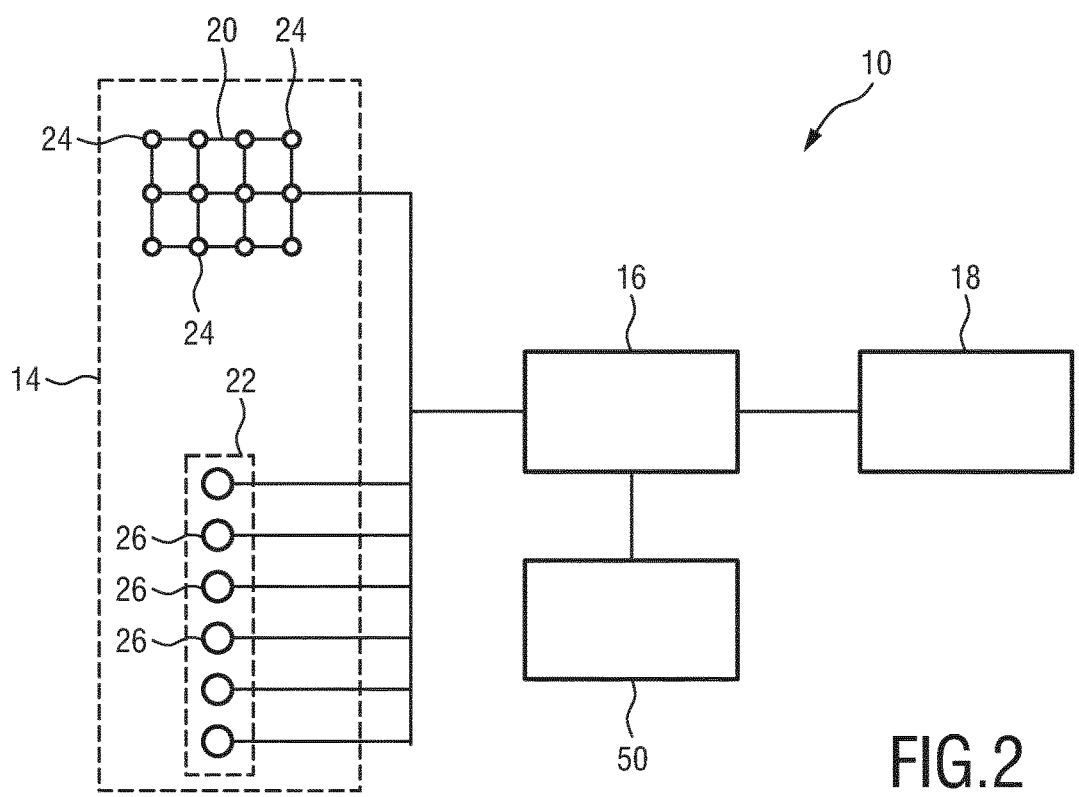
FIG. 2 shows a schematic block diagram of the first embodiment shown in FIG. 1.

FIG. 1 schematically shows a first embodiment of a system according to the present invention. The system is therein denoted in its entirety by reference numeral 10. FIG. 2 shows a block diagram which schematically illustrates the components of the system according to the first embodiment shown in FIG. 1 as well as their connections with each other.

The system 10 is preferably configured as a wearable system that may be worn or attached to a person 12. The system 10 comprises three main components: (i) a sensing component which is herein denoted as detection unit 14; (ii) a processing component which is herein denoted as analysis unit 16; and (iii) an actuator component which is herein denoted as feedback unit 18.

The detection unit 14 comprises one or more sensors for monitoring a cognitive and/or motoric activity of the person 12. These sensors, for example, monitor how and/or how much the person 12 is moving and/or they monitor the brain activity of the person 12. According to the first embodiment shown in FIGS. 1 and 2, the detection unit 14 comprises a brain activity sensor 20 for detecting a brain activity signal relating to the brain activity of the person 12 and a motion detection unit 22 for detecting a motion signal relating to a motion of one or more limbs of the person 12.

The brain activity sensor 20 is preferably realized as an electroencephalography (EEG) sensor which comprises a plurality of EEG electrodes 24. In the presented example shown in FIGS. 1 and 2 the EEG sensor 20 comprises twelve EEG electrodes. However, depending on the application, it may comprise an arbitrary number of EEG electrodes 24 (typically 10-24). These EEG electrodes 24 are configured to be attached to different positions on the scalp of the person 12. Each EEG electrode 24 thus records brain activity signals from a specific region of the brain of the person 12.

As an alternative to an EEG sensor, the brain activity sensor 20 may be realized as a functional MRI sensor. A still further alternative for measuring the brain activity of the person is the usage of one or more thermal sensors which are distributed over the scalp of the person 12 and configured to measure the brain activity indirectly by means of thermal sensing of the head. Such a thermal sensing of the head is based on the assumption that increased cognitive effort increases the blood flow and thereby the heat released by the specific part of the brain of the person 12. Of course, such an indirect sensing of the brain activity of the person 12 is much less sensitive and reliable compared to the usage of an EEG sensor as used in embodiment 1 shown in FIGS. 1 and 2 of the present application.

The motion detection unit 22 according to the first embodiment comprises a plurality of accelerometers 26. These accelerometers 26 are configured to be attached to the limbs of the person 12. In the exemplary embodiment shown in FIGS. 1 and 2, the motion detection unit 22 comprises six accelerometers 26, wherein two accelerometers 26 are attached to each leg of the person 12, and one accelerometer 26 is attached to each arm of the person 12. It shall be noted that this is only an example and that the motion detection unit 22 may of course comprise more or less accelerometers 26 depending on the desired sensing accuracy. The benefit of the accelerometer 26 is that they can be used when on the move, as they are on-body sensors. By means of the accelerometers 26 it is possible to monitor the motoric activity of the person 12, in particular the movement of the limbs of the person 12.

As an alternative or as an addition, the motion detection unit 22 may comprise one or more electromyography (EMG) sensors for sensing the electrical activity of the muscles and of the person 12. These EMG sensors are, similar as the accelerometers 26 preferably arranged at the limbs of the person 12.

The brain activity sensor 20 as well as the different sensors 26 of the motion detection unit 22 are connected to the analysis unit 16. The connections are shown in FIG. 1 by means of dotted lines. These data connections may either be realized as hard-wired connections or as wireless connections.

The analysis unit 16 preferably comprises a processor having software stored thereon which is adapted to process and interpret the signals acquired by the brain activity sensor 20 and the motion detection unit 22. The analysis unit 16 is particularly configured to determine, based on the detected brain activity signal provided by the brain activity sensor 20 and/or based on the motion signal provided by the motion detection unit 22, an activity level of the person 12 which is indicative of how many different motoric and/or cognitive tasks the person 12 is performing simultaneously. The analysis unit 16 in other words interprets the sensed signals in order to determine how many motoric and/or cognitive tasks the person 12 is performing concurrently. The brain activity signal of the brain activity sensor 20 may, for example, be analyzed to determine whether different monitored regions of the brain of the person 12 concurrently show an activity above a certain threshold. Alternatively, the brain activity signal provided by the brain activity sensor 20 may be analyzed to determine whether an enlarged activity occurs in a single region of the brain of the person 12. The motion signals of the motion detection unit 22 may be analyzed by the analysis unit 16 to determine an activity of the limbs of the person 12 in order to determine whether the person 12 is performing multiple motoric tasks at the same time (walking and waving the right hand at the same time). Specific examples of the signal analysis performed by the analysis unit 16 will be outlined further below in detail. The function of the signal analysis performed by the analysis unit 16 is to determine the activity level of the person 12, which activity level is an indicator of how many different tasks are performed by the person 12 concurrently. This is especially important since the presented system 10 focuses on supporting persons suffering from Parkinson's disease. Such persons shall be warned by the herein presented system 10 in case they are performing too many different motoric and/or cognitive tasks at the same time, since this significantly increases their risk of getting injured. As it has been outlined in the introductory portion of the description, Parkinson patients are at high risk of falling if they do not concentrate on walking, but do other things in parallel.

The system 10 uses the feedback unit 18 to provide a feedback to the person 12 which feedback shall warn the person 12 in the above-described situations. The feedback unit 18 is controlled by the analysis unit 16 and configured to provide the feedback to the person 12 if the analysis unit 16 determines an activity level of the person 12 which exceeds a predetermined threshold. The feedback unit 18 is preferably realized as a wearable component that may be worn by the person 12. In the presented example shown in FIG. 1, the feedback unit 18 is realized as a wearable component that may be worn on the wrist of the person 12. However, this is only considered to be an illustrative example. The feedback unit 18 may comprise several types of actuators, for example: (a) a sound actuator, such as a loudspeaker, for providing an audible feedback to the person 12; (b) a tactile actuator for providing a tactile feedback to the person 12 (e.g. by means of vibrations); (c) a display or light actuator for providing a visual feedback to the person 12.

According to a further embodiment (not specifically shown, the feedback unit 18 may also be combined in one device or arranged in the same casing together with the analysis unit 16. It would for example also be conceivable to use a smartphone or any other similar type of mobile computing device in which the analysis unit 16 and the feedback unit 18 may be integrated. The analysis unit 16 would in this case use the processor of the mobile computing device and could be implemented thereon in form of a software app. The feedback unit 18 could be part of the display, loudspeaker, and/or vibration alarm of the mobile computing device/smartphone.

In a still further alternative, the analysis unit 16 and/or the feedback unit 18 may be realized as external devices which are not directly attached to the person or worn by the person 12. In such cases it is preferred that the different components 14, 16, 18, 20, 22 of the system 10 are connected with each other by means of a wireless data connection.

Figure 3:
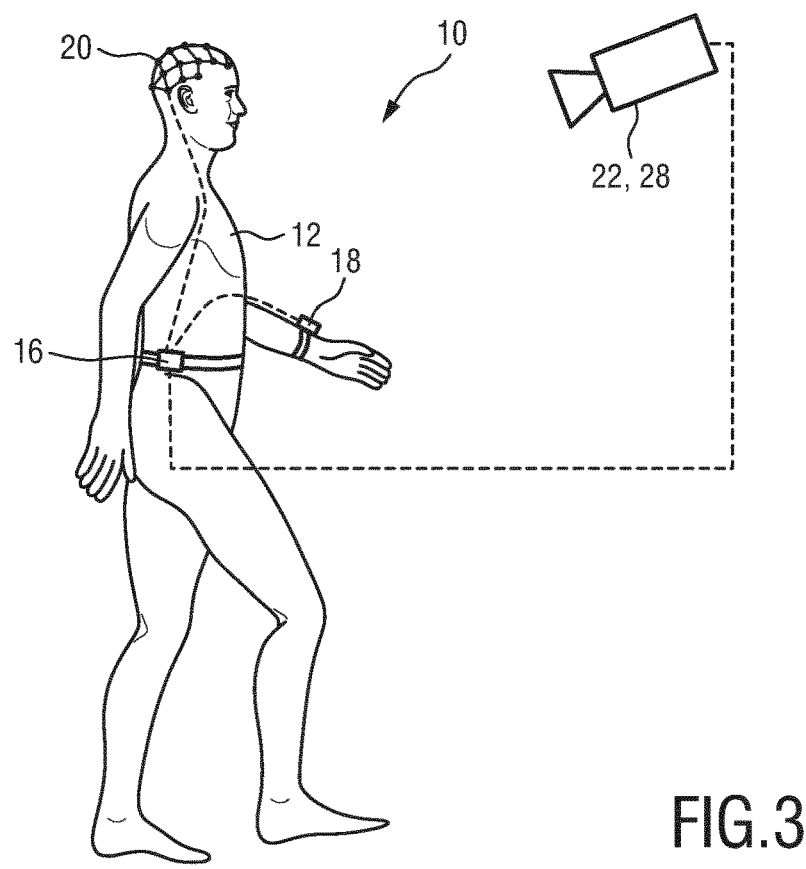
FIG. 3 shows a second embodiment of the system according to the present invention.
Figure 4:
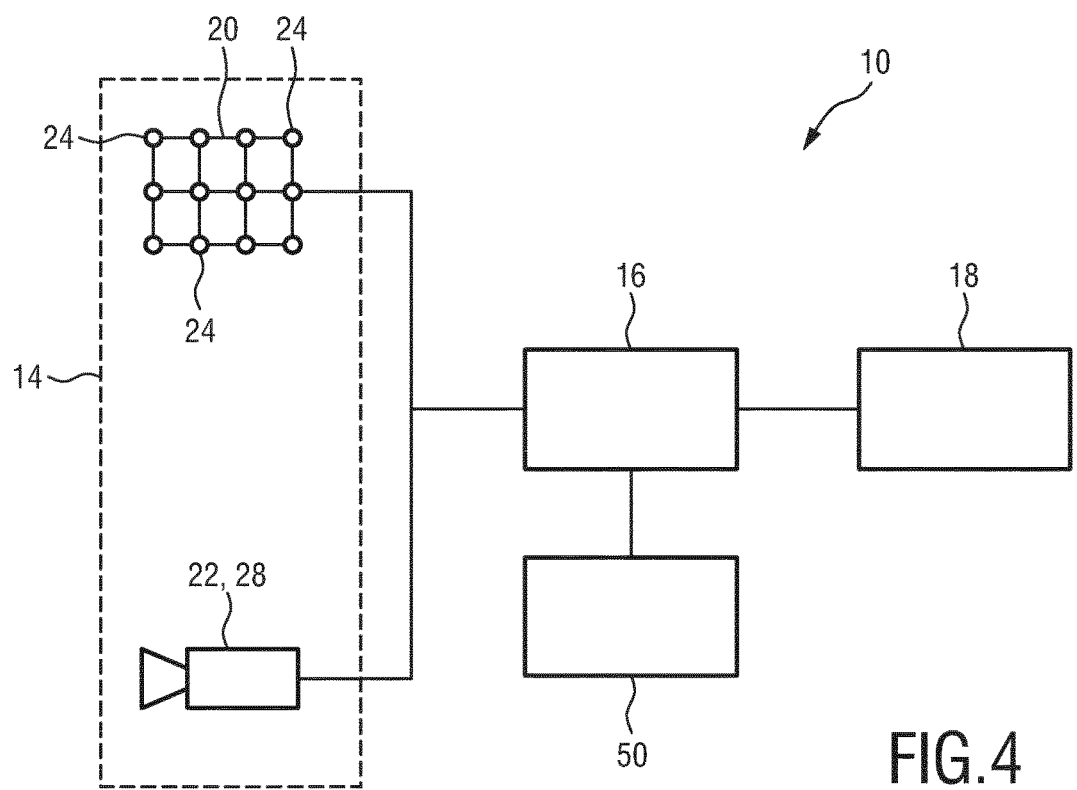
FIG. 4 shows a schematic block diagram of the second embodiment shown in FIG. 3.

FIGS. 3 and 4 show a second embodiment of the system 10. This second embodiment mainly differs from the first embodiment shown in FIGS. 1 and 2 in the way the motion detection unit 22 is realized. According to the second embodiment shown in FIGS. 3 and 4, the motion detection unit 22 is realized as an external component (not an on-body component). It comprises an optical motion sensor 28 which is configured to optically monitor how the person 12 is moving, in particular how the person 12 is moving his/her limbs. The optical motion sensor 28 preferably comprises a video camera that records the movements of the person 12 from outside. The remaining parts of the system 10 remain the same as explained with reference to the first embodiment shown in FIGS. 1 and 2 and are therefore not repeated again. It is to be noted that the first and second embodiments may also be combined with each other, such that the motion detection unit 22 comprises one or more accelerometers 26 and one or more video cameras or other optical motion sensors 28.

In the following, several exemplary embodiments shall be outlined on how the analysis unit 16 determines the activity level of the person 12 based on the detected brain activity signal(s) and/or the motion signal(s):

The analysis unit 16 may be configured to consider the activity level of the person as exceeding the predetermined threshold and to steer the feedback unit 18 to provide the feedback if a first one of the different signal components of the EEG signal which relates to the brain activity in a first region of the brain of the person 12 indicates a brain activity in said first region above a predetermined brain activity level. The activity level of the person 12 could, for example, be considered to exceed the predetermined threshold making it necessary to provide a feedback to the person 12 if the brain activity in the primary motor cortex is above a predetermined activity level that is specific for this region of the brain. The activity level of the person 12 could also be regarded as exceeding the predetermined threshold if the brain activity in the prefrontal cortex is above a predetermined brain activity level that is specific for this brain region.

Figure 7:
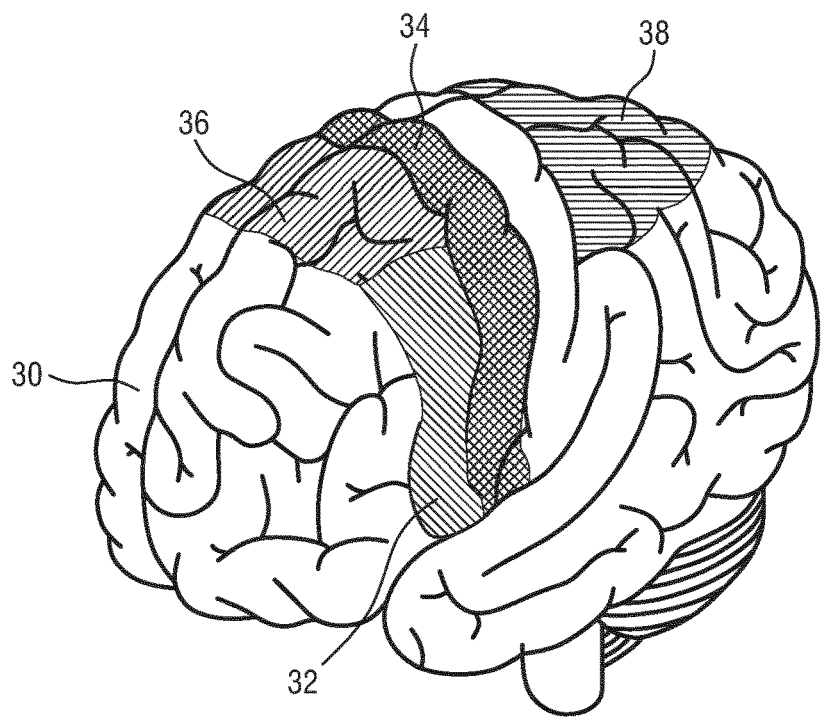
FIG. 7 schematically shows a human brain illustrating different brain regions.

FIG. 7 schematically shows the different regions of the human brain. The prefrontal cortex 30 is usually associated with decision making, reasoning, and the working memory as well as with the speech production. The premotor cortex 32 is a brain region which is typically active just before a movement is initiated (intention to perform a movement). The brain activity in the primary motor cortex 34 is usually associated with an ongoing motoric activity (movement). Further brain regions shown in FIG. 7 are the supplementary motor cortex 36 and the posterior parietal cortex 38. The supplementary motor cortex 36 is hypothesized to be associated with postural stabilization of the body, movement that involves coordination of both sides of the body and the control of sequences of movements. The posterior parietal cortex 38 is usually associated with the planning of movement w.r.t. effects on the orientation of the body and its environment.

The analysis unit 16 may also be configured to consider the activity level of the person 12 as exceeding the predetermined threshold and to steer the feedback unit 18 to provide the feedback if the brain activity in two brain regions 30, 38 is above a predetermined brain activity level (threshold). For example, the feedback (warning signal) may be output if the brain activity is simultaneously at a comparatively high level in the primary motor cortex 34 (responsible for ongoing motoric tasks) as well as in the prefrontal cortex 30 (responsible for ongoing cognitive tasks). This could be an indicator that the person 12 is not only moving, e.g. walking, but also thinking about a specific topic rather intensively.

In both above-mentioned examples it is preferred that the sensing of the motoric tasks the person 12 is performing is also supported and/or confirmed by means of the motion signal(s) detected by the motion detection unit 22.

The analysis unit 16 may also be configured to determine, based on the detected brain activity signal and/or the motion signal, whether the person 12 is walking. The activity level of the person 12 may in this case be considered as exceeding the predetermined threshold such that a feedback is provided, if it is determined that the person is not only walking, but simultaneously performing an additional motoric and/or cognitive task. The easiest way for the analysis unit 16 to determine whether the person 12 is walking is based on the motion signals provided by the accelerometers 26 that are attached to the legs and/or feed of the person 12. Detecting that the person 12 is performing another task concurrently to walking (e.g. waving his/her left or right hand or grabbing an item with his/her left or right hand) may be determined based on the accelerometers 26 attached to the arms and/or hands of the person 12. A brain activity sensor 20 is in this embodiment thus not necessarily needed.

Figure 5:
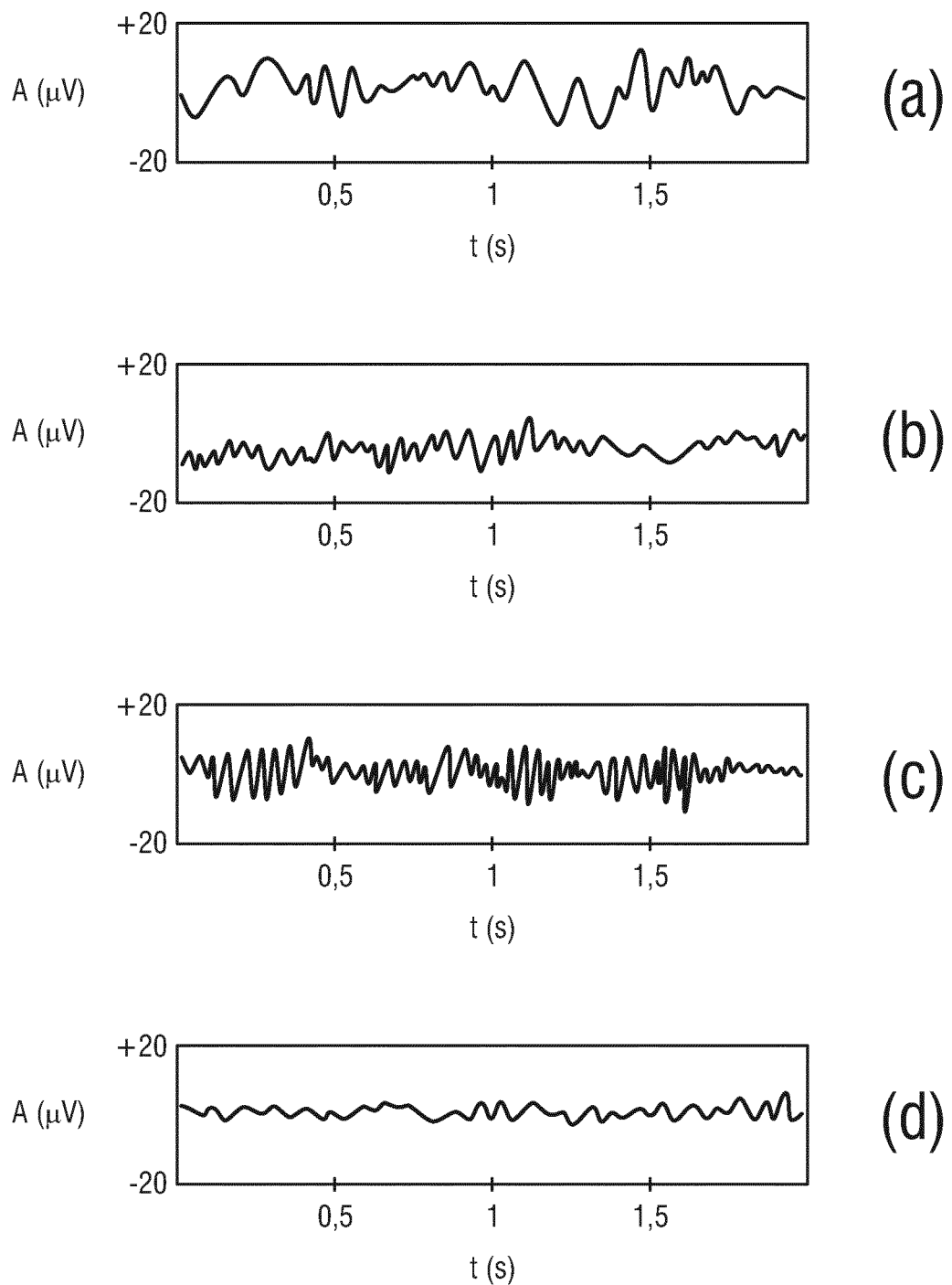
Figure 6:
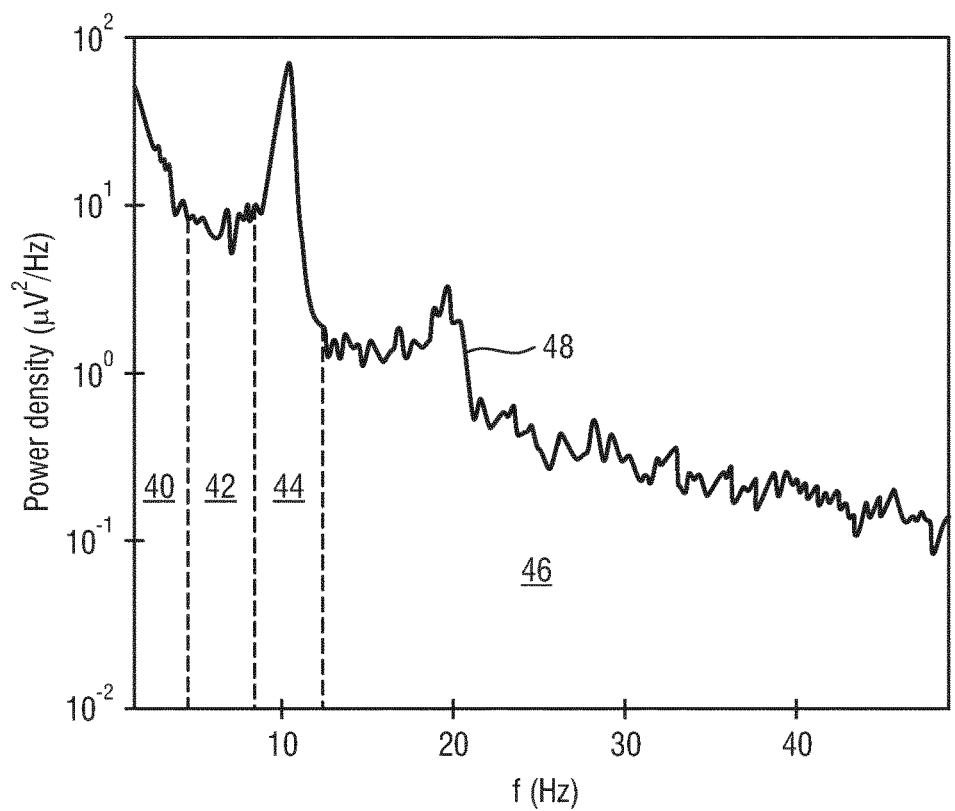
FIG. 6 shows an exemplary EEG signal in the frequency domain.

On the other hand, there are also embodiments conceivable in which the motion detection unit 22 is not necessarily needed. The activity level of the person 12 may also be determined by analyzing the EEG signal provided by the EEG sensor in one or more ranges of the frequency spectrum of the EEG signal. Such a frequency analysis of the EEG signal is preferably performed in the frequency domain. FIG. 5 shows an exemplary EEG signal in the time domain. FIG. 6 shows an exemplary EEG signal in the frequency domain. FIG. 5*a* shows the delta band of the EEG signal, i.e. the frequency range of 0.5-3.5 Hz. FIG. 5*b* shows the theta band of the EEG signal, i.e. the frequency range of 3.5-7 Hz. FIG. 5*c* shows the alpha band of the EEG signal, i.e. the frequency range of 7.5-12.5 Hz. FIG. 5*d* shows the beta band of the EEG signal, i.e. the frequency range of 12.5-40 Hz. The same frequency ranges are indicated in FIG. 6 by reference numerals 40-46 (delta band 40, theta band 42, alpha band 44, and beta band 46).

The analysis unit 16 may particularly be configured to inspect the frequency spectrum of the EEG signal 48 as follows: (1) the analysis unit 16 may be configured to determine the total power in the frequency spectrum related to the brain activity (0-100 Hz). High levels are expected in case of a high motoric and/or cognitive activity of the person 12. (2) The analysis unit 16 may also be configured to determine the power in the alpha band 44 and/or in the beta band 46. Low levels in the alpha band are expected in case of a high motoric and/or cognitive activity. High levels in the alpha band are instead usually associated with relaxation. High levels in the beta band are usually linked to active cognitive tasks.

Thus, the analysis unit 16 may be configured to consider the activity level of the person 12 as exceeding the predetermined threshold if at least one of (i) the signal power in the whole frequency spectrum of the EEG signal is above a predetermined threshold value, (ii) the signal power in the alpha band of the EEG signal is below a predetermined threshold value, and/or (iii) the signal power in the beta band of the EEG signal is above a predetermined threshold value.

The terms "power", "signal power" and "spectral power" are all meant to denote a measure which is determined by calculating the area under the curve of the frequency spectrum, e.g. by taking an integral over a certain frequency band.

However, it shall be pointed out again that specifically tasks performed by the person 12 concurrently while walking are considered to be critical. In other words, the analysis unit 16 may thus be configured to rank the task "walking" so high in the activity level that the activity level of the person 12 determined by the analysis unit 16 is always exceeded if walking is detected and any other cognitive and/or motoric task concurrently.

In all above-mentioned embodiments it is also preferred to compare the sensed signals (brain activity signal(s) and/or motion signal(s)) with reference signals that are acquired when the person 12 is relaxed. The system 10 therefore preferably also comprises a memory unit 50 in which such reference signals may be stored. This memory unit 50 may, for example, be realized as a hard drive or any other electronic storage means.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A system for supporting an elderly, frail and/or diseased person, wherein the system comprises:
    a detection unit including
        (i) a brain activity sensor configured to detect a brain activity signal relating to brain activity of the person and
        (ii) a motion detection unit configured to detect a motion signal relating to a motion of one or more body parts of the person;
    an analysis unit configured to
        determine, based on the detected brain activity signal and the detected motion signal, an activity level of the person which is indicative of how many different motoric and cognitive tasks the person is performing simultaneously, and
        determine, based on the detected brain activity signal and the detected motion signal, whether the person is walking; and
    a feedback unit configured to provide a feedback to the person the person is walking and the activity level of the person exceeds a predetermined threshold.

2. The system of claim 1, wherein the brain activity signal includes a plurality of different signal components each relating to the brain activity in a different region of the brain of the person, and the analysis unit is further configured to
    determine the activity level of the person by analyzing the different signal components in order to estimate how many different motoric and cognitive tasks the person is performing simultaneously.

3. The system of claim 2, wherein the analysis unit is further configured to
    consider the activity level of the person as exceeding the predetermined threshold and
    steer the feedback unit to provide the feedback after a first one of the different signal components which relates to the brain activity in a first region of the brain of the person indicates a brain activity in said first region above a first predetermined brain activity level.

4. The system of claim 2, wherein the analysis unit is further configured to consider the activity level of the person as exceeding the predetermined threshold and steer the feedback unit to provide the feedback after a first one of the different signal components which relates to the brain activity in a first region of the brain of the person indicates a brain activity in said first region above a first predetermined brain activity level and after simultaneously a second one of the different signal components which relates to the brain activity in a second region of the brain of the person indicates a brain activity in said second region above a second predetermined brain activity level.

5. The system of claim 1, wherein the brain activity sensor is an EEG sensor and the brain activity signal is an EEG signal, and wherein the analysis unit is further configured to determine the activity level of the person by analyzing the EEG signal in one or more ranges of the frequency spectrum of the EEG signal in the frequency domain.

6. The system of claim 5, wherein the analysis unit is further configured to analyze at least one of (i) a signal power in the whole frequency spectrum of the EEG signal, (ii) a signal power in the alpha band of the EEG signal, and (iii) a signal power in the beta band of the EEG signal.

7. The system of claim 6, wherein the analysis unit is further configured to consider the activity level of the person as exceeding the predetermined threshold and steer the feedback unit to provide the feedback after at least one of (i) the signal power in the whole frequency spectrum of the EEG signal is above a first threshold value, (ii) the signal power in the alpha band of the EEG signal is below a second threshold value, and/or (iii) the signal power in the beta band of the EEG signal is above a third threshold value.

8. The system of claim 1, wherein the analysis unit is further configured to
    consider the activity level of the person as exceeding the predetermined threshold, and
    steer the feedback unit to provide the feedback after it is determined, based on the detected brain activity signal and the detected motion signal, that the person is walking and simultaneously performing an additional motoric and/or cognitive task.

9. The system of claim 1, further comprising:
    a memory unit configured to store a reference brain activity signal and/or a reference motion signal, wherein the analysis unit is further configured to
    determine the activity level of the person by comparing the detected brain activity signal and the detected motion signal with the reference brain activity signal and/or reference motion signal, respectively.

10. The system of claim 1, wherein the motion detection unit comprises one or more accelerometers.

11. The system of claim 1, wherein the motion detection unit comprises an optical motion sensor.

12. The system of claim 1, wherein the motion detection unit comprises an electromyography sensor.

13. The system of claim 1, wherein the feedback unit comprises at least one of
    (i) a loudspeaker configured to provide audible feedback to the person,
    (ii) a display or light actuator configured to provide visual feedback to the person, and
    (iii) a tactile actuator configured to provide tactile feedback to the person.

14. A method for supporting an elderly, frail and/or diseased person, wherein the method comprises:
    receiving a brain activity signal relating to the brain activity of the person;

receiving a motion signal relating to a motion of one or more body parts of the person;

determining, based on the detected brain activity signal and the detected motion signal, an activity level of the person which is indicative of how many different motoric and cognitive tasks the person is performing simultaneously;

determining, based on the detected brain activity signal and the detected motion signal, whether the person is walking; and providing a feedback to the person after the person is walking and the activity level of the person exceeds a predetermined threshold.

15. A non-transitory computer-readable medium comprising instructions for causing a computer to carry out a method of providing feedback to a person, the non-transitory computer-readable medium comprising:

instructions for receiving a brain activity signal relating to the brain activity of the person;

instructions for receiving a motion signal relating to a motion of one or more body parts of the person;

instructions for determining, based on the detected brain activity signal and the detected motion signal, an activity level of the person which is indicative of how many different motoric and cognitive tasks the person is performing simultaneously;

instructions for determining, based on the detected brain activity signal and the detected motion signal, whether the person is walking; and instructions for providing the feedback to the person after the person is walking and the activity level of the person exceeds a predetermined threshold.

* * * * *